United States Patent [19]

Eschenfelder et al.

[11] Patent Number: 4,944,943

[45] Date of Patent: Jul. 31, 1990

[54] MIXTURE OF A SUBSTANCE HAVING THROMBOLYTIC ACTIVITY AND OF AN ANTITHROMBOTIC SUBSTANCE

[75] Inventors: Volker Eschenfelder, Wiesloch; Bernhard Schmied, Frankenthal; Klaus Ruebsamen, Neustadt, all of Fed. Rep. of Germany

[73] Assignee: BASF Aktiengesellschaft, Ludwigshafen, Fed. Rep. of Germany

[21] Appl. No.: 309,299

[22] Filed: Feb. 13, 1989

[30] Foreign Application Priority Data

Feb. 13, 1988 [DE] Fed. Rep. of Germany ....... 3804600

[51] Int. Cl.$^5$ .................... A61K 37/547; A61K 35/62
[52] U.S. Cl. .............................. 424/94.64; 424/94.63; 514/2; 514/21
[58] Field of Search .................... 424/94.63, 94.64, 95; 514/2, 21, 56

[56] References Cited

U.S. PATENT DOCUMENTS 3,432,596  3/1969  Markwardt .................... 530/858
4,190,574  2/1980  Svendsen ..................... 530/331

FOREIGN PATENT DOCUMENTS 0041766  9/1988  European Pat. Off. .

OTHER PUBLICATIONS

Blyuger et al., cited in Chem. Abstracts, vol. 102:179077e, (1985).
*Journal of the International Society on Thrombosis and Haemostasis*, (1986), vol. 55, pp. 28–34, "Effect of a Selective Thrombin Inhibitor MCI-9038 on Fibrinolysis In Vitro and In Vivo", Y. Tamao et al.

Primary Examiner—Jacqueline Stone
Attorney, Agent, or Firm—Oblon, Spivak, McClelland, Maier & Neustadt

[57] ABSTRACT

A mixture of a substance having thrombolytic activity and of an antithrombotic substance which is suitable for controlling vascular disorders caused by thrombosis is described.

7 Claims, No Drawings

MIXTURE OF A SUBSTANCE HAVING THROMBOLYTIC ACTIVITY AND OF AN ANTITHROMBOTIC SUBSTANCE

The present invention relates to a mixture of protein active substances for controlling vascular disorders caused by thrombosis.

It has already been disclosed that t-PA (tissue plasminogen activator) leads, by activation of plasminogen, to the dissolution of fibrin and thus to the reperfusion of thrombosed vessels (European Laid-Open Application 41,766). It has also been disclosed that it is possible by concurrent adminstration of a selecctive antithrombotic substance (=thrombin antagonist) such as MCI 9038 (=(2R,4R)-4-methyl-1[N²-[(3-methyl-1,2,3,4-tetrahydro-8-quinolinyl)-sulfonyl]-L-arginyl]-2-piperidinecarboxylic acid) or heparin considerably to reduce the time necessary for Lysis of a thrombosed blood vessel, in that further deposition of fibrin on the existent thrombus is prevented (Thrombosis & Haemostasis 56 (1986) 28).

The present invention relates to a mixture of a substance having thrombolytic activity and of an antithrombotic substance.

Substances having thrombolytic activity are those which dissolve blood clots. They include prourokinase (PUK), urokinase (UK), streptokinase (SK) and t-PA substances. The designation t-PA substances denotes t-PA itself as well as the polypeptides which have t-PA activity and are derived therefrom by substitution, modification and/or deletion of one or more amino acids or by chain-shortening. These substances may be in glycosylated or non-glycosylated form. Polypeptides of these types are mentioned, for example, in the following patents and patent applications:

| DE | 3,011,956 | EP | 93,619 |
|---|---|---|---|
|  | 3,240,174 |  | 124,613 |
|  | 3,502,760 |  | 152,736 |
|  | 3,537,176 |  | 155,388 |
| GB | 2,173,804 |  | 174,835 |
|  |  |  | 178,105 |
| WO | 84/01786 |  | 184,363 |
|  | 86/01538 |  | 196,920 |
|  |  |  | 198,015 |

The designation antithrombotic substance includes all substances which prevent or impede the development of blood clots. These include, in particular, hirudin and the polypeptides which have hirudin activity and are derived therefrom by substitution, modification and/or deletion of one or more amino acids or by chain-shortening. These substances can be in glycosylated or non-glycosylated or in sulfated and non-sulfated form. Substances of these types are described, for example, in the following patents:

| DE | 3,445,517 | EP | 158,986 |
|---|---|---|---|
|  | 3,526,995 |  | 168,342 |
| FR | 8,404,755 |  | 171,024 |
|  | 8,506,672 |  | 200,655 |
| WO | 85/04418 |  |  |
|  | 86/06406 |  |  |

The ingredients of the mixtures can also be in the form of acid addition salts. Suitable acid addition salts are, in particular, physiologically tolerated salts with customary acids which can be used therapeutically; inorganic acids which may be mentioned are the hydrohalic acids such as hydrochloric acid, as well as sulfuric acid and phosphoric or pyrophosphoric acid; primarily suitable organic acids are sulfonic acids such as benzene- or p-toluenesulfonic acid or lower alkanesulfonic acids such as methanesulfonic acid, as well as carboxylic acids such as acetic acid, lactic acid, palmitic and stearic acid, malic acid, tartaric acid, ascorbic acid and citric acid. Since the ingredients of the mixtures also contain amino acid residues with free carboxyl groups, they may also be in the form of a metal salt, in particular as an alkali metal or alkaline earth metal salt, for example sodium, potassium, calcium or magnesium salt, or else as ammonium salt, derived from ammonia or a physiologically tolerated organic nitrogenous base. They can also be in the form of an internal salt.

The substance having thrombolytic activity and the antithrombotic substance are present in the mixture in amounts in the ratio of from 10:1 to 500:1, preferably 50:1 to 100:1.

The mixture can be administered in the form of a solution intraarterially, intravenously or subcutaneously, preferably by infusion. Besides the active substances, the solution normally also contains a buffer, for example a phosphate buffer intended to maintain the pH between about 3.5 and 7, and, furthermore, sodium chloride, manitol or sorbitol to adjust to isotonicity. They can be in freeze-dried or dissolved form and contain a preservative having antibacterial activity.

It is possible with the aid of the new combination to dissolve thromboses more rapidly and safely than solely with substances having thrombolytic activity. This is suprising inasmuch as antithrombotic substances have no thrombolytic activity. It is furthermore possible by combined use of the two substances to reduce distinctly the frequency of reocclusion after lysis of an existent thrombus. The mixture is therefore suitable for the treatment of thromboses of any type, such as thrombophlebitis, hemorrhoidal thrombosis, pulmonary embolism and infarct.

The amount of the mixture which is given to the patient per therapy is such that the total amount of substance having thrombolytic activity which is administered is between 50 and 100 mg per patient.

Administration is complete after 2 hours as a rule.

EXAMPLE A

Preparation of a solution 1 g of t-PA and 15 mg of hirudin (HV 2 specified in EP 158,564) are dissolved in 100 ml of 0.1M sodium phosphate buffer of pH 6.0. Sodium chloride is then added to the solution to produce a solution isotonic with blood. The solution is sterile filtered and dispensed into 5 ml ampoules.

EXAMPLE B

Demonstration of the effect

Anesthetized rabbits are immobilized supine on a temperature-controlled support and, after tracheotomy, artifically ventilated. PE catheters are tied into the carotid artery and jugular vein to measure the blood pressure and to infuse t-PA, respectively. Another catheter for pressure measurement is tied into the right femoral artery. Then the right and left external iliac arteries are exposed as far as the junction to the abdominal aorta. A short segment of the abdominal aorta is freed of surrounding tissue and provided with an electromagnetic flow-measuring device (Gould). Then, with the aid of a PE catheter, a copper spiral is advanced through the left iliac artery into the abdominal aorta. After the spiral has been released from the catheter it is picked up by the bloodstream and carried into the right iliac artery. The catheter is removed and then the left iliac artery is tied off. A thrombus forms in the region of the spiral within a short time. The time and extent of the occlusion of the femoral artery caused by this are determined from the fall in pressure measured distal from the spiral and from the reduction in blood flow in the abdominal aorta.

30 min after occlusion of the vessel by the thrombus, rt-PA is administered intravenously as a bolus (80 μg/kg), followed by an infusion of 8 μg/kg. min. Concurrently with the infusion of rt-PA, r-hirudin is administered, likewise as infusion. The t-PA infusion is terminated after reperfusion lasting at least 10 min is achieved, but after 2 h at the latest. The infusion of hirudin is not terminaed until after completion of the 3-hour experimental period. In the animals where reperfusion occurs within 2 h, the time after completion of the T-PA infusion until reocclusion occurs is determined.

The effect of r-hirudin on the thrombolytic action of recombinant t-PA was determined on a thrombus induced in the iliac artery by a copper spiral. A further investigation was of whether and to what extent r-hirudin is able to prevent reocclusion of the vessel after successful lysis.

Complete stable occlusion of the vessel took place a mean of $8.4 \pm 0.5$ min (n=24) after the copper spiral was positioned in the iliac artery. There was no noteworthy effect on the heart rate and mean blood pressure by this manipulation.

In 7 of 12 animals the infusion of rt-PA led to recanalization of the occluded blood vessel after a mean of $75.3 \pm 6.8$ (Tab. 1). In 5 animals the infusion was discontinued without success after 2 h. These experiments were not included in the further evaluation.

However, with rt-PA in the same dosage but in combination with r-hirudin the thrombus was dissolved completely in 9 of 12 animals. The mean time up to reperfusion was $69.1 \pm 4.2$ min.

After successful lysis and after discontinuation of the t-PA infusion there was reocclusion of the opened blood vessel in all the animals after a mean of $21.9 \pm 4.2$ min. The first signs of incipient reocclusion are cyclic flow variations (CFV), which occurred only a few minutes after the end of infusion (Tab. 1).

It was possible with r-hirudin in combination with rt-PA to prevent completely reocclusion after successful lysis in seven animals, while reocclusion in 2 animals did not occur until after 35 and 45 min. No cyclic flow variations were observed.

The data obtained show:

It was possible by combining t-PA with r-hirudin to increase the frequency with which reperfusion of occluded blood vessels was achieved from 58 to 75%.

r-Hirudin resulted in a significant decrease in the frequency of reocclusion after successful lysis.

r-Hirudin completely prevented the occurrence of cyclic blood flow variations attributable to the formation of local platelet aggregates.

TABLE 1

Thrombolysis and reocclusion time after intravenous administration of rt-PA or rt-PA in combination with r-hirudin in rabbits with a thrombus induced in the iliac artery by a copper spiral.

| Animal No. | Time before reperfusion (min) | Reocclusion time | No. of cyclic flow variations | Blood flow in the iliac artery (ml/min) | | |
|---|---|---|---|---|---|---|
| | | | | Initial value | After copper spiral | After reperfusion |
| rt-PA | | | | | | |
| 1 | 56 | 8 | 5 | 51 | 20 | 27 |
| 2 | * | — | — | 98 | 24 | — |
| 3 | 79 | 36 | 4 | 67 | 29 | 12 |
| 4 | * | — | — | 111 | 9 | — |
| 5 | 79 | 10 | 6 | 99 | 12 | 11 |
| 6 | 111 | 36 | 7 | 98 | 21 | 27 |
| 7 | 72 | 19 | 0 | 90 | 30 | 12 |
| 8 | 70 | 21 | 0 | 67 | 48 | 48 |
| 9 | * | — | — | 32 | 14 | — |
| 10 | * | — | — | 90 | 84 | — |
| 11 | 60 | 23 | 0 | 27 | 13 | 17 |
| 12 | * | — | — | 75 | 66 | — |
| x ± SEM | 75.3 ± 6.8 | 21.9 ± 4.2 | 3.1 ± 1.2 | 75.3 ± 7.9 | 30.8 ± 6.8 | 22.0 ± 5.1 |
| rt-PA + hirudin (0.1 mg/kg · h) | | | | | | |
| 13 | * | — | — | 83 | 8 | — |
| 14 | 50 | 35 | 0 | 66 | 57 | 53 |
| 15 | 57 | >60 | 0 | 150 | 84 | 21 |
| 16 | 49 | >60 | 0 | 83 | 23 | 17 |
| 17 | 77 | >60 | 0 | 30 | 5 | 8 |
| 18 | * | — | — | 27 | 0 | — |
| 19 | * | — | — | 40 | 0 | — |
| 20 | 80 | >60 | 0 | 40 | 17 | 17 |
| 21 | 95 | >60 | 0 | 33 | 20 | 25 |
| 22 | 85 | >60 | 0 | 36 | 10 | 8 |
| 23 | 47 | >60 | 0 | 33 | 10 | 10 |
| 24 | 22 | 45 | 0 | 72 | 21 | 15 |
| x ± SEM | 69.1 ± 4.2 | | | 57.8 ± 10.3 | 22.7 ± 9.0 | 19.3 ± 4.6 |

*no reperfusion within 120 min.

We claim:

1. A pharmaceutical composition for the treatment of thrombosis, which consists essentially of:
   (a) an amount of prourokinase, urokinase, streptokinase or t-PA or a polypeptide having t-PA activity effective for dissolving thrombosis or a combination thereof, or the pharmaceutically acceptable salts thereof, and
   (b) an amount of hirudin or a hirudin derivative effective for preventing or impeding the development of blood clots or a combination thereof, or the pharmaceutically acceptable salts thereof.

2. The pharmaceutical composition as claimed in claim 1, wherein said substance having thrombolytic activity and said substance having antithrombotic activity is used in the composition in a ratio of about 10:1 to 500:1, respectively.

3. The pharmaceutical composition as claimed in claim 2, wherein said ratio is about 50:1 to 100:1.

4. The pharmaceutical composition as claimed in claim 1, which is in the form of a solution, and further contains a buffer effective for maintaining the pH of the solution between about 3.5 and 7.

5. The pharmaceutical composition as claimed in claim 1, which consists essentially of t-PA and hirudin.

6. A method of treating vascular disorders caused by thrombosis in a patient suffering therefrom, which comprises administering to said patient an effective amount of the pharmaceutical composition of claim 1.

7. The method as claimed in claim 6, wherein between about 50 to 100 mg of said substance having thrombolytic activity is administered per patient.

* * * * *